United States Patent
Kang et al.

(10) Patent No.: US 8,283,736 B2
(45) Date of Patent: Oct. 9, 2012

(54) HYDROGEN ION SENSING DEVICE USING OF ARRAYED GATED LATERAL BJT

(75) Inventors: Shin Won Kang, Daegu (KR); Hyurk Choon Kwon, Yeongju-si (KR); Se Hyuk Yeom, Daegu (KR)

(73) Assignee: Kyungpook National University Industry Academic Cooperation, Daegu-si (KR)

( * ) Notice: Subject to any disclaimer, the term of this patent is extended or adjusted under 35 U.S.C. 154(b) by 29 days.

(21) Appl. No.: 13/031,208

(22) Filed: Feb. 19, 2011

(65) Prior Publication Data

US 2011/0204455 A1 Aug. 25, 2011

(30) Foreign Application Priority Data

Feb. 19, 2010 (KR) .......................... 10-2010-0015058

(51) Int. Cl.
*H01L 29/73* (2006.01)
(52) U.S. Cl. .............................. 257/414; 257/E29.174
(58) Field of Classification Search .................. 257/414, 257/E29.174
See application file for complete search history.

*Primary Examiner* — Benjamin Sandvik
*Assistant Examiner* — Whitney T Moore
(74) *Attorney, Agent, or Firm* — Revolution IP, PLLC (57) ABSTRACT

A hydrogen ion sensing device of the present invention includes: a reference electrode; a sensing portion which senses hydrogen ions by contacting an ion aqueous solution; and a plurality of ring-like lateral bipolar junction transistors, each including a lateral collector, an emitter, a vertical collector and a floating gate connected to the reference electrode, with the emitter surrounded by the floating gate and the lateral collector, wherein the plurality of ring-like lateral bipolar junction transistors are formed on a common substrate and are connected in parallel.

6 Claims, 10 Drawing Sheets

HYDROGEN ION SENSING DEVICE USING OF ARRAYED GATED LATERAL BJT

BACKGROUND OF THE INVENTION

1. Field of the Invention

The present invention relates to an ion sensing device, and more particularly, to a hydrogen ion sensing device using an arrayed gated lateral bipolar junction transistor of a MOS hybrid mode having highly-improved ion sensitivity.

2. Description of the Related Art

Hydrogen ions have various kinds of electrolytes which are required for the industrial world as well as the livelihood of the organisms and have their respective constant ranges of concentrations during support of life. pH is a factor critical in understanding a chemical reaction and a chemical property of substance. In particular, pH is a parameter critical in determining a property of a solution containing a target of measurement. A pH sensor is required to make a quantitative measurement of pH.

Such a pH measurement is the first step in determining a chemical property of substance as well as controlling a chemical reaction. The pH measurement is currently in wide use for many applications including the water-related industries, chemical industries, public health, agriculture, fishing industries, biology-related industries, etc.

As examples of sensors used to measure pH (power of hydrogen) which is a logarithm of hydrogen ion concentration, ISE (Ion Selective Electrode), ISFET (Ion Selective Field Effect Transistor), LAPS (Light Addressable Potentiometric Sensor) and so on are mainly being studied.

In recent years, a new concept of semiconductor devices used to make a measurement of hydrogen ion concentration has been reported. Representative examples may include semiconductor devices employing a charge transfer technique and a GaAs AlGaN/GaN HEMT technique. These studies are different from typical studies to improve sensitivity using new sensing materials based on an intrinsic FET theory or improve stability by adding particular peripheral circuits.

Such recent studies show results beyond the limit of physical sensitivity and Nernst sensitivity of sensing portions. As an extension of these studies, there is a need for development of devices exhibiting new electrical characteristics using established silicon-based MOS technologies for exploitation of new applications, and development of new electronic devices implementing high sensitivities.

SUMMARY OF THE INVENTION

In the light of the above circumstances, it is an object of the invention to provide an efficient ion sensing device which is capable of controlling ion sensitivity using a base current as well as a gate with an emitter voltage fixed, so that the ion sensitivity is about 8 times as high as that of a single gated lateral BJT, and which is capable of operating in a first quadrant even in an n-well process of a commercial p-substrate, unlike ISFET implemented in a p-well of an existing n-substrate, to allow for electrical compatibility, which results in significant reduction of production costs.

To achieve the above object, according to an aspect of the invention, there is provided a hydrogen ion sensing device including: a reference electrode; a sensing portion which senses hydrogen ions by contacting an ion aqueous solution; and a plurality of ring-like lateral bipolar junction transistors, each including a lateral collector, an emitter, a vertical collector and a floating gate connected to the reference electrode, with the emitter surrounded by the floating gate and the lateral collector, wherein the plurality of ring-like lateral bipolar junction transistors are formed on a common substrate and are connected in parallel.

Preferably, the sensing portion includes: a multi-layered metal film connected to the floating gate via a via contact; and a passivation layer formed on the metal film. Preferably, the passivation layer includes a silicon oxide layer and a silicon nitride layer.

Preferably, the transistor is a PNP or NPN type lateral bipolar junction transistor (LBJT). Preferably, the device is selectively driven in a BJT mode or a MOS mode depending on a polarity of the base current.

Preferably, the polarity of the base current is negative and the device uses an ambient current as a pilot signal to monitor an operation of the device if a potential ($V_{RG}$) of the reference electrode is negative.

According to one embodiment, an operation point can be adjusted by the gate voltage, like the existing ISFET, and also the operation point can be adjusted by the bases current with the emitter voltage fixed. Polarities of values of X and Y axes are positive in comparison with a p-channel MOSFET driven with the common collector setting and the device can be operated in a linear region (an active mode) in comparison with ISFET operating in a saturation region.

The ion sensitivity is about 8 times as high as that of the single gated lateral BJT and can be adjusted by the gate voltage. Further, the device is capable of operating in a first quadrant even in an n-well implemented in a p-substrate in a commercial CMOS process, which results in significant reduction of production costs.

The device outputs a pH value in the form of a current, which is robust to external noises. In addition, a voltage format measurement can be made by changing a threshold voltage depending on pH as conventional, where a pilot signal can be used due to an output component of a bipolar device, which is useful in signal processing.

Recent applications for detecting biomaterials require devices having a large sensing area. To meet such requirements, an MOSFET-based CHEMFET may be manufactured to provide a large aspect ratio with a violation of a design rule. However, for a gated lateral BJT, if a sensing area of a device is increased, in addition to a violation of a design rule, emitter efficiency is deteriorated as a base width is increased, and only an area occupied in a die is increased without increase of sensitivity. To overcome these problems, an arrayed gated lateral BJT of the present invention is used to achieve two objects, i.e., improvement of sensitivity and adaptation to a large area.

DETAILED DESCRIPTION OF PREFERRED EMBODIMENTS

Hereinafter, preferred embodiments of the present invention will be described in detail with reference to the drawings.

Figure 1:
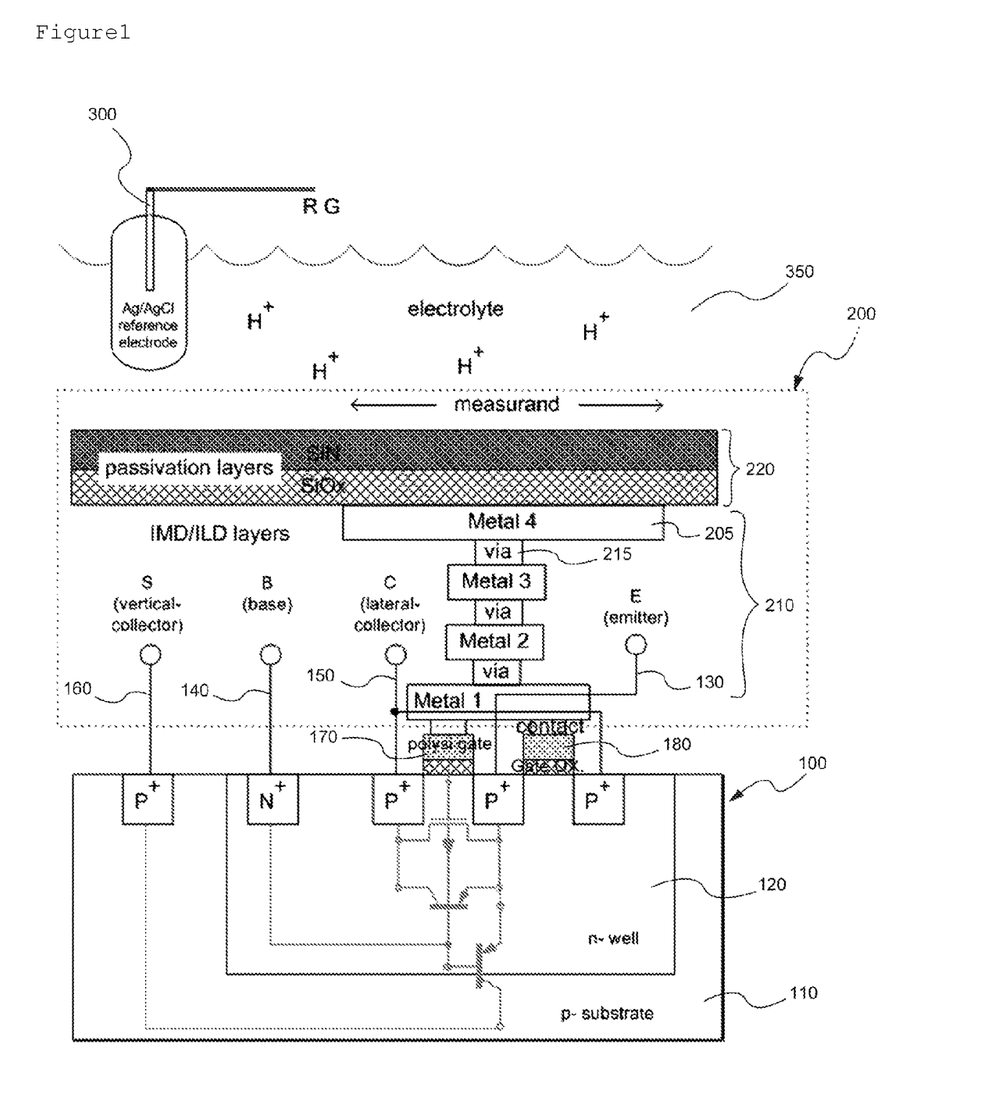
FIG. 1 is a view illustrating a structure of a hydrogen ion sensing device using an arrayed gated lateral bipolar junction transistor according to an embodiment of the present invention.
Figure 2:
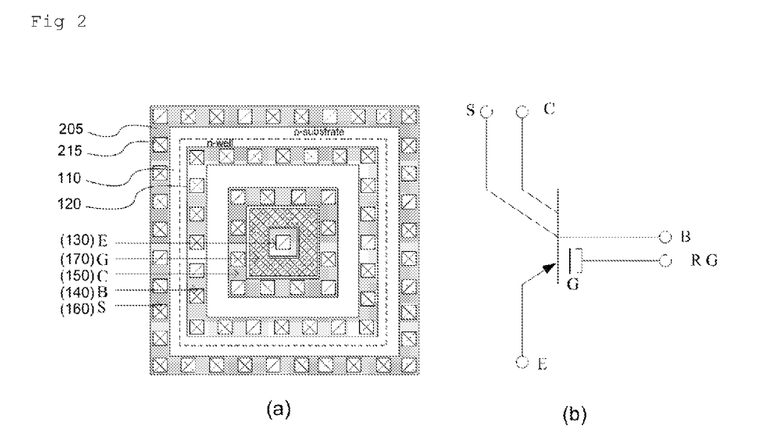
FIG. 2 shows a layout of the arrayed gated lateral bipolar junction transistor used for the hydrogen ion sensing device according to the embodiment.
Figure 3:
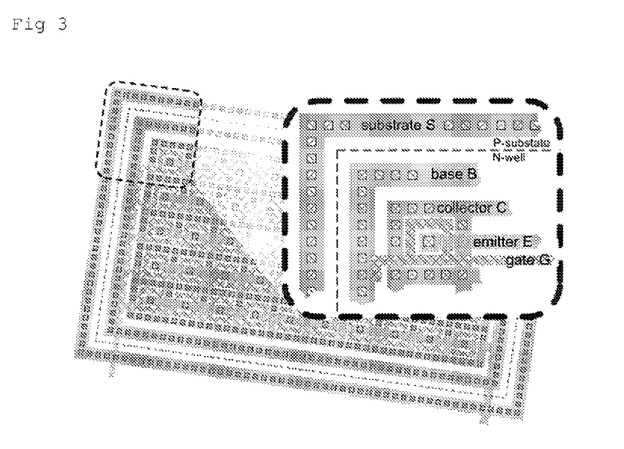
FIG. 3 shows a layout of an arrayed gated lateral bipolar junction transistor type hydrogen ion sensing device having a parallel structure according to an embodiment of the present invention.

FIG. 1 is a view illustrating a structure of a hydrogen ion sensing device using an arrayed gated lateral bipolar junction transistor according to an embodiment of the present invention, FIG. 2 shows a layout of the arrayed gated lateral bipolar junction transistor used for the hydrogen ion sensing device according to the embodiment, and FIG. 3 shows a layout of an arrayed gated lateral bipolar junction transistor type hydrogen ion sensing device having a parallel structure according to an embodiment of the present invention.

As shown in FIG. 1, according to an embodiment of the invention, an arrayed gated lateral bipolar junction transistor 100 is constructed by forming an N well 120 in a P type substrate 110, forming P+ doping regions n the N well 110, and forming a lateral collector 150 and an emitter 130 in the P+ doping regions, respectively. Thus, the arrayed gated lateral bipolar junction transistor 100 has a structure where a quadrilateral ring-like gate and the lateral collector 150, which surround the emitter 130, are formed. In addition, a base 140 is formed in an N+ doping region surrounding the lateral collector 150 and a P+ doping region serving as a substrate contact in FET is formed in the lateral of the P type substrate 110 outside the N well region 120 to thereby a vertical collector 160.

A hydrogen ion sensing device 200 is formed on a base region of the above-configured arrayed gated lateral bipolar junction transistor. The hydrogen ion sensing device 200 has a structure where the sensing device 200 is connected to the gate 180 through a via contact 215. The sensing device 200 includes a plurality of metal layers 210 and an ion sensitive passivation layer 220 formed on the uppermost metal layer 205.

The top surface of the passivation layer 220 contacts an ion aqueous solution 350 in which a reference electrode 300 is provided to be connected to the floating gate 180 of the arrayed gated lateral bipolar junction transistor, thereby completing the hydrogen ion sensing device 200.

Hereinafter, embodiments of the hydrogen ion sensing device 200 as configured above and results of experiments on the hydrogen ion sensing device 200 will be described in detail.

Up to now, most studies on ion sensing devices has been focused on a primary transducer, such as material selection of a sensing film, for the purpose of increase of sensitivity. However, the present invention is focused on a secondary transducer which is driven in a bipolar mode or a MOS hybrid mode other than a MOS mode.

The hydrogen ion sensing device of the present invention includes an LBJT structure (secondary transducer) required to be driven in the MOS hybrid mode, and a floating gate (primary transducer) which is required to adopt a conventional CMOS process, is covered with a passivation layer (SiN/SiOx), and is operated as an ion detection gate.

Unlike an open gate form, the present invention is designed to connect the gate to the final metal layer through a contact via and use the metal layers and silicon nitride for passivation as an ion sensing portion. With the design using this technique, a gate width can be applied to a nono-sized process.

A bipolar property of a gated lateral bipolar junction transistor (gated LBJT), which is a device manufactured in a commercial process, may be implemented with no change in its objectivity and commercial CMOS process, as will be described below.

Experiments and Methods

A single device according to an embodiment of the present invention has a 1poly-4metal structure manufactured in a 0.35 μm standard logic production process. A layout of a designed final chip is shown in FIG. 3. A die is designed to have a dimension of 5 mm by 5 mm. Each pin has a protection circuit as a MOSFET type ESD circuit for device protection. It is to be understood by those skilled in the art that such a chip size logic method may be designed and modified in various different ways.

FIG. 2 shows a plane layout of a gated LBJT as a single p channel transistor device implemented by an N-well COMS technology applied to embodiments of the present invention. The device includes five terminals, i.e., a lateral collector C, a base B, an emitter E, a vertical collector S, and a floating gate G coupled to a reference electrode RG via an electrolyte.

The emitter E is a single contact surrounded by the rectangular ring-like collector C to improve an emitter efficiency, which is one difference comparable to an aspect ratio (W/L) in a source-drain of LSFET (with the emitter E surrounded by the collector C).

A base width (corresponding to a channel length L of CMOS) located between the emitter and a current is defined by a 0.5 μm polysilicon gate and the minimal base width (the minimal L) is limited by a used process.

The rectangular ring-like floating gate located on the base region is connected to the final metal layer M4 via a contact and a Via. The metal layer M4 of a 16×16 μm area sets a sensing area and reduces an error due to light.

Silicon nitride including a silicon dioxide layer is used as a pH sensing portion. This is a passivation layer which is located on the metal layer M4 and is deposited by PECVD in a commercial CMOS process.

The single device occupies an area of 22 μm by 22 μm and an arrayed device occupies a die area of 39 μm by 57 μm. As shown in FIG. 3, the hydrogen ion sensing device of the present invention is configured to connect 50 single gated LBJT devices in parallel. The devices are arranged with multiple emitters in order to obtain a light lateral current efficiency. Here, each emitter dot surrounded by the polysilicon gate has the minimal p-diffusion contact.

The sensing device includes an array of 5×10 gated lateral BJT connected in parallel in order to increase ion sensitivity.

Since carriers injected into the lateral collector from the emitter through the base are mostly collected in the lateral, a collector current is directly proportional to the perimeter of the emitter. Due to such a current flow characteristic, a layout design for collecting lateral carriers is required to improve a current gain β. In the present invention, a high current efficiency is achieved using a multi-emitter dot structure, that is, by increasing a perimeter-to-surface ratio of the emitter.

On the other hand, in a case of open gate, a device having a large sensing region occupies a large channel length and width. However, a size of unit device in the aspect ratio is strictly limited by a design rule provided by a foundry of a modern commercial process. According to the present invention, the multi-emitter dot structure introduced in the layout may be considered to have an equivalently large area. In addition, when a measurement is made using a device having a large sensing region on the gate in an aqueous solution, a device having the multi-emitter dot structure can distribute an electric field and capacitive load in an electrolyte over gates of unit devices. This device occupies an arrayed device of 39 μm×57 μm and a gate length of each single emitter dot is 0.5 μm.

Hydrogen Ion Measurement

Electrical characteristics and pH sensing characteristics of the device of the present invention are measured by a semiconductor parameter measuring instrument. Power required for device operation is also supplied from the parameter measuring instrument. In the device, portions except the hydrogen ion sensing portion are sealed with epoxy after chips on a printed circuit board (PCB) are bonded, and measurement for electrical and optical shielding is made in a metal barrel called a test fixture.

Electrical characteristics are measured using a dummy device included in design. The dummy device (dummy LBJT) has the same geometrical structure as the device of the present invention except the gate connected with a line to apply a voltage instead of the reference electrode. This may exclude a nonlinear measurement error, which may occur in a measurement in an aqueous solution, thereby showing correct electrical characteristics.

An actual response characteristic is measured in an aqueous solution using the device of the present invention. A circuit equivalent to a measurement arrangement is shown in FIG. 1. The device of the present invention is driven in a forward active mode between an emitter (source) and a collector (drain). In consideration of a characteristic of the gate lateral BJT applied to a well, a common collector setting is adopted to bias the device. The reason for this is that the common collector setting provides a larger positive output signal that a common emitter setting.

As shown in FIG. 1, the Ag/AgCl reference electrode is biased to form inversion or storage of a channel through a gate potential VRG and a bias is applied by a gate bias common collector setting of the device.

Results and Considerations

Figure 4:
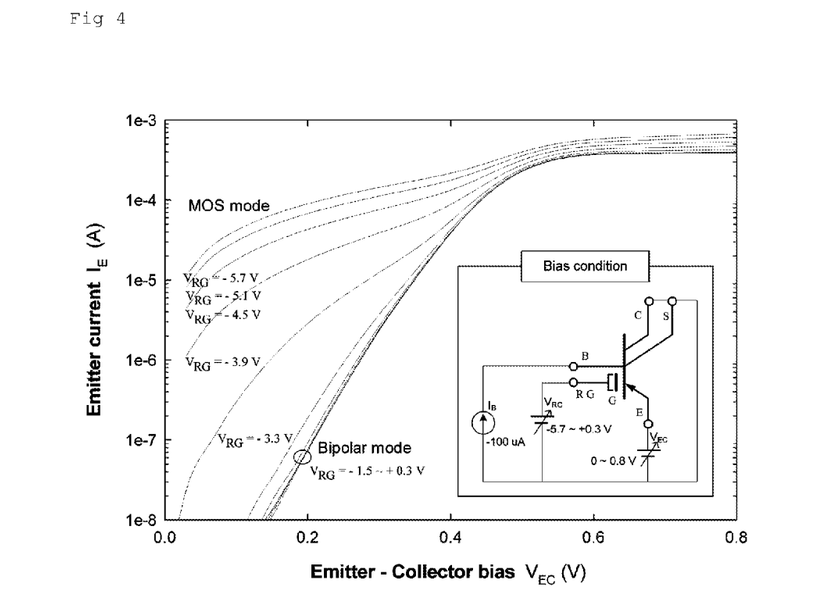
FIG. 4 is a graph showing bias setting and measurement results for the hydrogen ion sensing device according to the embodiment.

FIG. 4 is a graph showing bias setting and measurement results for the hydrogen ion sensing device of the present invention. FIG. 4 shows a relationship between an emitter current and a voltage when an emitter-collector bias voltage is varied from 0 to 0.8 V, a reference electrode voltage is varied by 0.6 V from −5.7 V to −3.3 V in an MOSFET mode and a reference electrode voltage is varied by 0.6 V from −1.5 V to +0.3 V in a BJT mode if a base current is fixed at −100 μA in a buffer solution having a value of pH 10. The result shows that the device can operate from the MOSFET mode to the BJT mode depending on a voltage applied to the reference electrode electrically coupled to the floating gate. When a negative voltage is applied to the reference electrode, the result shows an MOSFET property.

Considering an ash-colored equivalent circuit shown in FIG. 1, the emitter current $I_E$ is equivalent to the sum of a vertical collector current $I_S$ and a lateral collector current $I_C$. The lateral collector current $I_C$ is greatly affected by a gate voltage which causes a drain current of MOSFET dependant on an EIS (Electrolyte Insulator Semiconductor) structure in consideration of a potential difference for pH.

When a voltage is positively increased, all curves converge on a thick curve shown in the right side in the graph and the sensing device shows a typical lateral BJT characteristic that the device operates at $V_{EC}$ of more than 0.2 V. It is hard for this pure bipolar operation to be used for pH sensing, which is because $I_E$ is unaffected by a gate bias and $I_C$ does not include a drain current $I_D$ of MOSFET if the gate voltage has a positive value. Here, a measured current gain is 4.

pH Response Characteristic of Single Hydrogen Ion Sensing Device

The Ag/AgCl reference electrode is biased to form inversion or storage of a channel through the gate potential $V_{RG}$. The device is immersed in an aqueous solution and is applied with a bias with a common collector setting.

Figure 5:
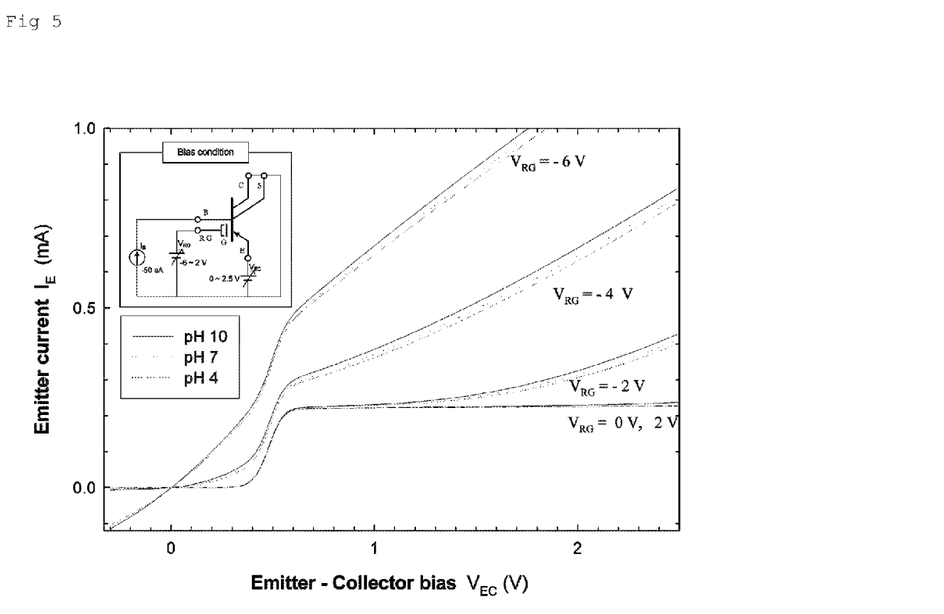
FIG. 5 is a graph showing a voltage/current characteristic depending on change in a gate voltage for a single hydrogen ion sensing device according to an embodiment of the present invention.

FIG. 5 is a graph showing a voltage/current characteristic depending on change in a gate voltage for a single hydrogen ion sensing device according to an embodiment of the present invention. As shown in FIG. 5, in order to verify a pH sensing characteristic of the device, with a base current fixed at −50 μA, the reference voltage is gradually varied by 2 V from −6 V to +2 V and a pH value is changed from 4 to 10. When $V_{EC}$ is 2 V and $V_{RG}$ is −4 V, a pH response is about 6.18 μA/pH.

Figure 6:
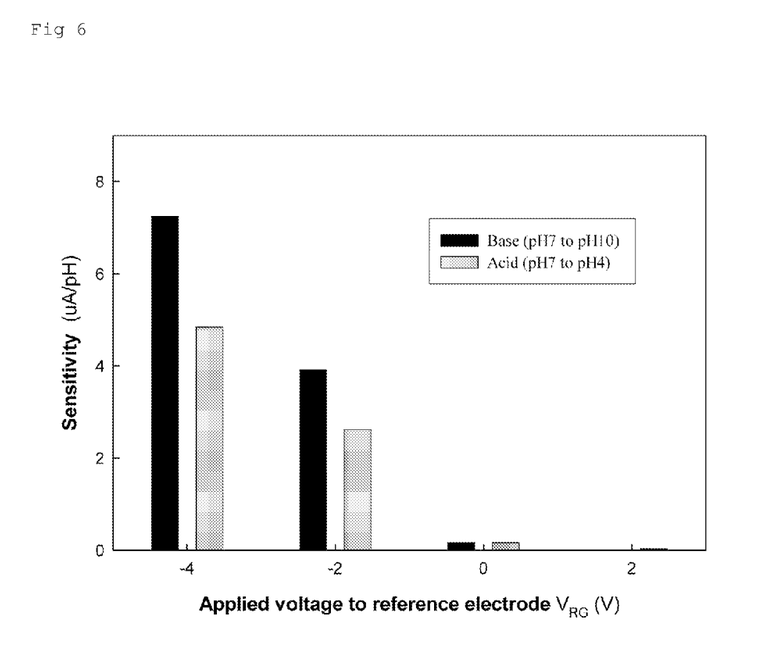
FIG. 6 is a graph showing a relationship between acid and base sensitivities when $V_{EC}$=2 V and $I_B$=−50 μA for a single hydrogen ion sensing device according to an embodiment of the present invention.

FIG. 6 is a graph showing a relationship between acid and base sensitivities when $V_{EC}$=2 V and $I_B$=−50 μA for a single hydrogen ion sensing device according to an embodiment of the present invention. Here, sensitivities are high when $V_{RG}$ has a negative value and have difficulty in distinguishing therebetween. This is because $I_E$ does not include the drain current $I_D$ caused by hydrogen ions except a bipolar current component.

Figure 7:
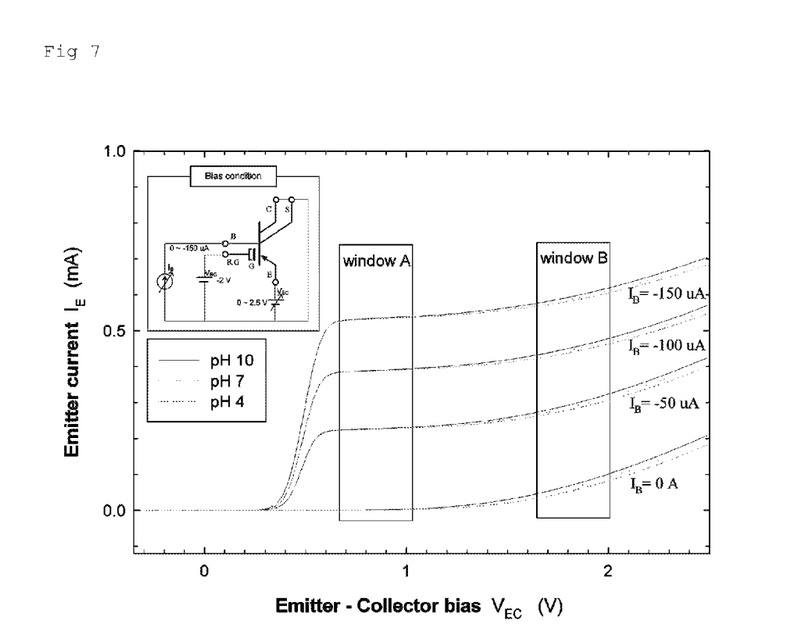
FIG. 7 is a graph showing a voltage/current characteristic depending on change in a base current for a single hydrogen ion sensing device according to an embodiment of the present invention.

FIG. 7 is a graph showing a voltage/current characteristic depending on change in a base current for a single hydrogen ion sensing device according to an embodiment of the present invention. As shown in FIG. 7, in order to verify a well controlling effect characteristic, with a reference electrode voltage fixed at −2 V, a base current is gradually varied from 0 to −150 μA while changing a pH value from 4 to 10. When $V_{EC}$ is 2 V and $I_B$ is −50 μA, a pH response is 3.175 μA/pH and an offset voltage, which does not appear in a FET device, is 0.34 V. As shown in FIG. 7, no pH difference is detected in a window A where an emitter current is constant irrespective of change of a pH value. On the other hand, a pH value can be detected in a window B where an emitter current is varied depending on change of a pH value.

pH Response Characteristic of Arrayed Gated Hydrogen Ion Sensing Device 50 gated lateral BJTs in the embodiment of the present invention are compared with a single gated lateral BJT in various kinds of ion solutions. A bias is set in a common collector mode in order to operate in a first quadrant and gates of devices connected to each other are capacitively coupled to a reference electrode. In order to investigate device characteristics in an electrolyte, the devices are immersed in buffer solutions of pH 4, pH 7 and pH 10.

Figure 8:
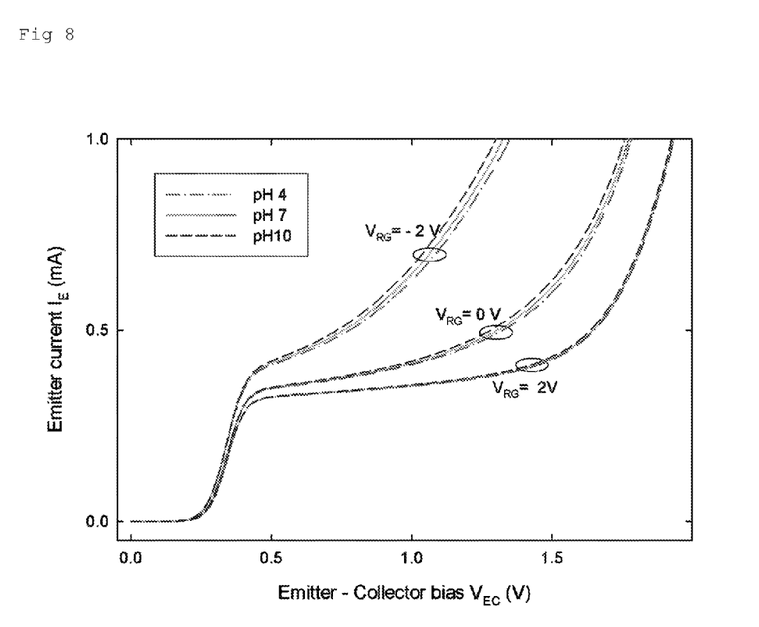
FIG. 8 is a graph showing a voltage/current characteristic when $I_B$=−20 μA and pH=4, 7 and 10 for a hydrogen ion sensing device according to an embodiment of the present invention.

FIG. 8 is a graph showing a voltage/current characteristic when $I_B$=−20 μA and pH=4, 7 and 10 for a hydrogen ion sensing device according to an embodiment of the present invention. With a bias current fixed at −20 μA in a base terminal, the emitter voltage $V_{EC}$ is biased between 0 and 2 V and a reference electrode is biased between −2 V and +2 V at a 2 V interval. As shown in FIG. 8, the devices show triode-like and pentode-like characteristics depending on a gate potential in the common collector setting. The devices show the triode-like characteristic when a negative bias causing increase of β of BJT is applied to the gate. This characteristic means extension of a channel and increase of the current $I_C$ including pH concentration information.

For a positive gate bias, that is, in a bipolar mode, a triode-like characteristic is observed. This characteristic means reduction of a channel, i.e., reduction of pH sensitivity, and also means that the devices have variable sensitivity depending on the gate bias.

Figure 9:
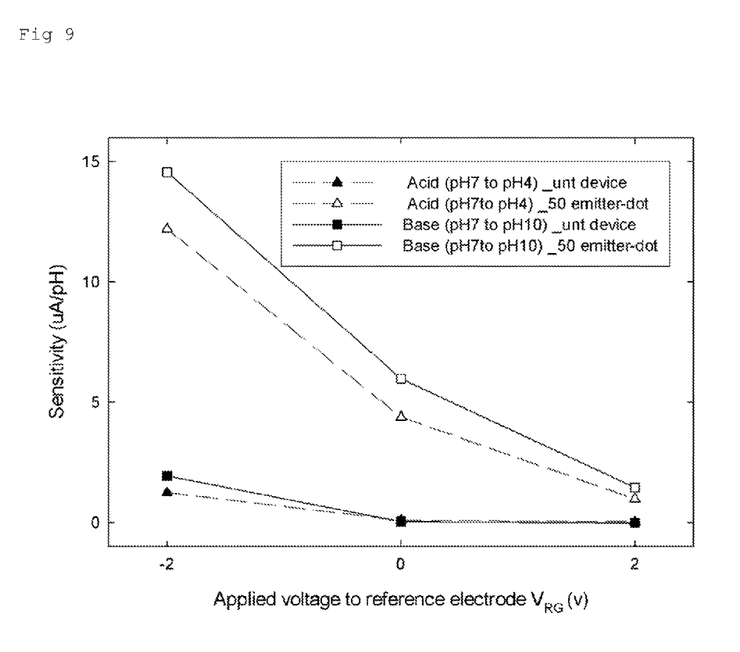
FIG. 9 is a graph showing a relationship between acid and base sensitivities for single and arrayed hydrogen ion sensing devices according to an embodiment of the present invention.

FIG. 9 is a graph showing a relationship between acid and base sensitivities for single and arrayed hydrogen ion sensing devices according to an embodiment of the present invention. As shown in FIG. 9, when $V_{EC}$ is 1.5 V and $V_{RG}$ is −2 V, average sensitivity of 50 emitter dots is 13.38 μA/pH and sensitivity of the single device is 1.58 μA/pH. That is, the sensitivity of 50 emitter dots is eight times as high as the sensitivity of the single device. This characteristic means reduction of a channel, i.e., reduction of pH sensitivity, and also means that the devices have variable sensitivity depending on the gate bias.

Figure 10:
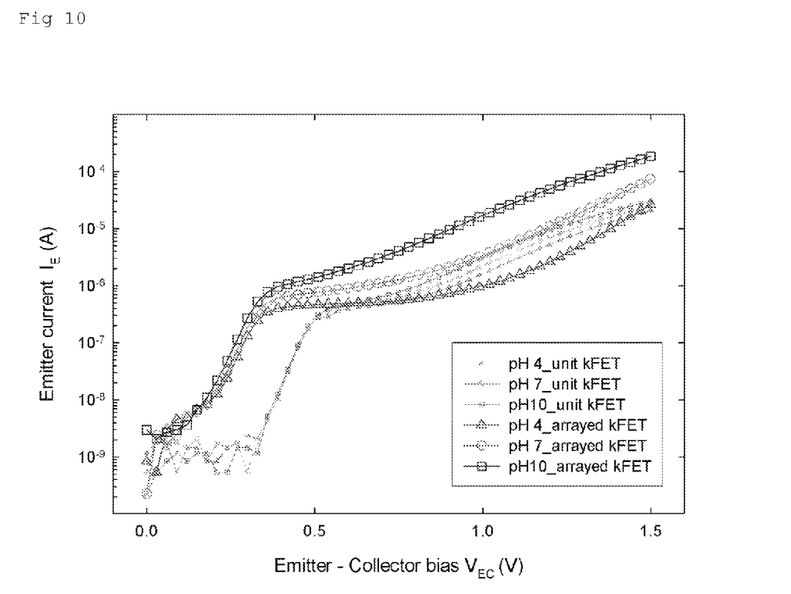
FIG. 10 is a graph showing a comparison between an arrayed hydrogen ion sensing device of the present invention and a single hydrogen ion sensing device upon changing a base current.

FIG. 10 is a graph showing a comparison between an arrayed hydrogen ion sensing device of the present invention and a single hydrogen ion sensing device upon changing a base current. As shown in FIG. 10, in order to verify characteristics of a single hydrogen ion sensing device and an arrayed gated hydrogen sensing device of the present invention, measurements are made with a reference electrode voltage fixed at 0 V and a current fixed at 0 A. This is a technique used to prevent instability of bias which may occur if a replaced solution does not contact a reference electrode sensing portion for measurement with an increased reference voltage or current.

With change of a pH value from 4 to 10, when a reference electrode bias $V_{RG}$ is −2 V, the sensitivity of the single device is 0.287 μA/pH and the sensitivity of the arrayed device of the present invention is 2.99 μA/pH which is about 11 times as high as the sensitivity of the single device.

Figure 11:
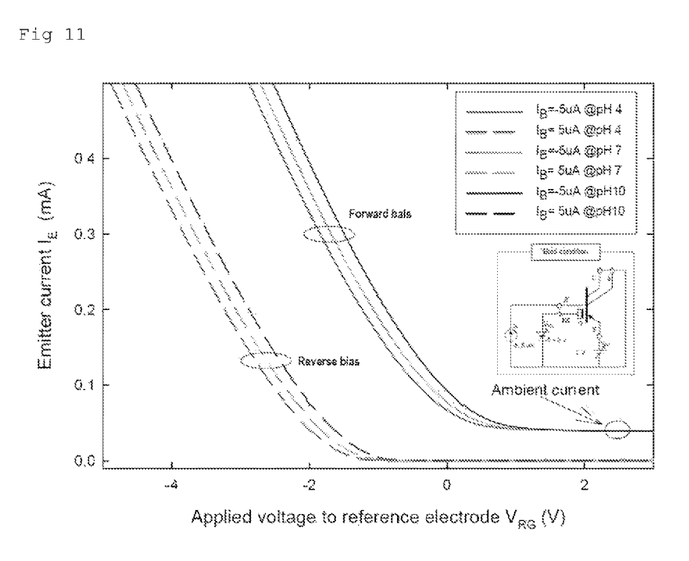
FIG. 11 is a graph showing a pH detection characteristic depending on a polarity of a base current.

FIG. 11 is a graph showing a result of measurement using a change in a threshold voltage depending on pH as in a conventional method. The graph of FIG. 11 shows a result of an MOS component with a BJT characteristic removed by applying a reverse bias to a well and a substrate when a base current has a positive value. This is driven using the same measuring method as the existing ISFET. On the other hand, when the base current has a negative value and a forward bias is applied to the well and the p substrate, this is driven in an MOS-hybrid mode if $V_{RG}$ has a negative value. If $V_{RG}$ has a positive value, it is possible to obtain an ambient current having a BJT component including no pH information. This ambient current may be used as a pilot signal to monitor an operation of the devices. In this case, the pilot signal can be used due to an output component of a bipolar device, which is useful in signal processing.

In this manner, the operation point of the hydrogen ion sensing device of the present invention can be controlled by a voltage applied to the reference electrode, like ISFET, as well as the base current with the emitter voltage fixed.

In addition, since the device of the present invention is operated in the MOS hybrid mode, it electrically acts as a depletion type NMOSFET while it is physically an enhancement type PMOSFET.

From the above results, it can be seen that polarities of values of X and Y axes are positive in comparison with a p-channel MOSFET driven with the common collector setting and the device is operated in a linear region (an active mode) in comparison with ISFET operating in a saturation region.

In consideration of a relationship between a pH value and a value of an output signal $I_E$ (for example, $I_E$ of the suggested device or a drain current of ISFET), the suggested device has a direct proportional relationship, whereas ISFET based on NMOSFET has an inverse proportional relationship.

In order to increase ion sensitivity, 50 gated lateral BJTs are compared with a single gate lateral BJT in various kinds of ion solutions. When measurements are made in an applied bias setting, the hydrogen ion sensing device of the present invention shows ion sensitivity which is about 8 times or more as high as that of the single gated lateral BJT. It is noted in the above that this ion sensitivity can be controlled by the base current and the gate voltage.

From the standpoint of production cost, the above results mean that the device of the present invention can be operated in the first quadrant even in an n-well while the existing ISFET incurs high production costs since it has to use an additional p-well process or triple-well to be operated in the first quadrant using a commercial p-type substrate.

Although a few exemplary embodiments have been shown and described, it will be appreciated by those skilled in the art that adaptations and changes may be made in these exemplary embodiments without departing from the spirit and scope of the invention, the scope of which is defined in the appended claims and their equivalents.

What is claimed is:

1. A hydrogen ion sensing device comprising:
    a reference electrode;
    a sensing portion which senses hydrogen ions by contacting an ion aqueous solution; and
    a plurality of ring-like lateral bipolar junction transistors, each including a lateral collector, an emitter, a vertical collector and a floating gate connected to the reference electrode, with the emitter surrounded by the floating gate and the lateral collector,
    wherein the plurality of ring-like lateral bipolar junction transistors are formed on a common substrate and are connected in parallel.

2. The hydrogen ion sensing device according to claim 1, wherein the sensing portion includes:
    a multi-layered metal film connected to the floating gate via a via contact; and
    a passivation layer formed on the metal film.

3. The hydrogen ion sensing device according to claim 2, wherein the passivation layer includes a silicon oxide layer and a silicon nitride layer.

4. The hydrogen ion sensing device according to claim 1, wherein the transistor is a PNP or NPN type lateral bipolar junction transistor (LBJT).

5. The hydrogen ion sensing device according to claim 1, wherein the device is selectively driven in a BJT mode or a MOS mode depending on a polarity of the base current.

6. The hydrogen ion sensing device according to claim 5, wherein the polarity of the base current is negative and the device uses an ambient current as a pilot signal to monitor an operation of the device if a potential ($V_{RG}$) of the reference electrode is negative.

* * * * *